(12) United States Patent
Shepard et al.

(10) Patent No.: US 7,531,349 B1
(45) Date of Patent: May 12, 2009

(54) STANDOFF BIOAGENT-DETECTION APPARATUS AND METHOD USING MULTI-WAVELENGTH DIFFERENTIAL LASER-INDUCED FLUORESCENCE

(75) Inventors: James G. Shepard, Palos Verdes Estates, CA (US); Kalin Spariosu, Thousand Oaks, CA (US)

(73) Assignee: Raytheon Company, Waltham, MA (US)

( * ) Notice: Subject to any disclaimer, the term of this patent is extended or adjusted under 35 U.S.C. 154(b) by 379 days.

(21) Appl. No.: 10/756,553

(22) Filed: Jan. 13, 2004

(51) Int. Cl.
*C12M 1/34* (2006.01)
*C12M 3/00* (2006.01)
*G01N 21/64* (2006.01)
*G01J 1/58* (2006.01)
*A61B 6/02* (2006.01)

(52) U.S. Cl. .................. 435/288.7; 435/808; 422/82.08; 422/82.05; 250/461.1; 250/462.1; 250/461.2; 250/459.1; 250/483.1; 378/42; 378/45

(58) Field of Classification Search .............. 435/288.7, 435/808; 422/82.08, 82.05; 250/461.1, 462.1, 250/461.2, 459.1, 483.1; 378/42, 45
See application file for complete search history.

(56) References Cited

U.S. PATENT DOCUMENTS

| | | | | |
|---|---|---|---|---|
| 4,490,043 A | * | 12/1984 | Cramp | 356/407 |
| 6,313,471 B1 | * | 11/2001 | Giebeler et al. | 250/458.1 |
| 6,653,971 B1 | * | 11/2003 | Guice et al. | 342/54 |
| 6,911,344 B1 | * | 6/2005 | Reichert et al. | 436/518 |
| 6,930,775 B1 | * | 8/2005 | Spremo et al. | 356/328 |
| 2001/0025930 A1 | * | 10/2001 | Engelhardt et al. | 250/459.1 |
| 2002/0175294 A1 | * | 11/2002 | Lee et al. | 250/458.1 |
| 2003/0098422 A1 | * | 5/2003 | Silcott et al. | 250/458.1 |
| 2003/0160182 A1 | * | 8/2003 | Petrich et al. | 250/458.1 |
| 2003/0230728 A1 | * | 12/2003 | Dai et al. | 250/458.1 |
| 2005/0207943 A1 | * | 9/2005 | Puzey | 422/82.05 |

* cited by examiner

*Primary Examiner*—William H Beisner
*Assistant Examiner*—Nathan A Bowers
(74) *Attorney, Agent, or Firm*—Leonard A. Alkov

(57) ABSTRACT

A standoff bioagent-detection apparatus and method use a direct ultraviolet source to detect bioagents. In some embodiments, a standoff bioagent-detection apparatus and method use laser-induced fluorescence to determine the presence of a biological agent having an aromatic-protein shell, such as Tryptophan. In some embodiments, multi-wavelength differential laser-induced fluorescence helps reduce false alarm caused by naturally occurring interferants. In some embodiments, a full range of ultraviolet wavelengths is initially simultaneously generated to fluoresce Tryptophan to determine if an ambient level is excessive. When the ambient level is excessive, individual ultraviolet wavelengths may be generated in differential pairs and the detected fluorescence levels may be correlated with atmospheric absorption levels for Tryptophan to determine if a bioagent is highly likely to be present.

6 Claims, 4 Drawing Sheets

STANDOFF BIOAGENT-DETECTION APPARATUS AND METHOD USING MULTI-WAVELENGTH DIFFERENTIAL LASER-INDUCED FLUORESCENCE

TECHNICAL FIELD

Embodiments of the present invention pertain to bioagent detection using ultraviolet fluorescence.

BACKGROUND

With the increasingly greater threat of biological weapons, it is desirable to provide a warning when bioagents are present. The presence of bioagents within the air or at a particular location may indicate the presence of a biological threat, as well as the possible deployment of a biological weapon. Many conventional bioagent-detection systems have an unacceptably high false-alarm rate. The use of such conventional systems may result in unnecessary precautions and possibly panic.

Many conventional systems for detecting bioagents are also large and cumbersome, and some systems use a point-detection scheme. Some of these systems include point sensors which generally require large collection devices, such as air concentrators, that operate within the presence of a potential biological threat.

Some other conventional bioagent-detection systems utilize standoff detection techniques, which attempt to detect the presence of a bioagent from a distance. Many of these standoff detection systems are large and cumbersome, some have poor efficiency, and some are generally not robust enough for field use.

Thus there are general needs for systems and methods that provide improved bioagent detection. There are also needs for improved standoff bioagent-detection systems and methods that permit bioagent detection without the need to be present within the potential biological threat. There are also needs for bioagent-detection systems and methods that are more accurate and have a low false-alarm rate. There are also needs for bioagent-detection systems and methods that are compact, more efficient and robust, and may be implemented in hand-held devices.

SUMMARY

A standoff bioagent-detection system and method use a direct ultraviolet source for bioagent detection. In some embodiments, a standoff bioagent-detection system and method use laser-induced fluorescence of an aromatic protein, such as Tryptophan, to determine the presence of a biological agent having an aromatic-protein shell. In some embodiments, multi-wavelength differential laser-induced fluorescence helps reduce false alarms caused by naturally occurring interferants. In some embodiments, a full range of ultraviolet wavelengths is initially simultaneously generated to induce fluorescence in an aromatic protein to determine if an ambient level is excessive. When the ambient level is excessive, individual ultraviolet wavelengths may be generated in differential pairs and the detected fluorescence levels may be correlated with atmospheric absorption levels for the aromatic protein to determine if a bioagent is highly likely to be present.

BRIEF DESCRIPTION OF THE DRAWINGS

The appended claims are directed to some of the various embodiments of the present invention. However, the detailed description presents a more complete understanding of embodiments of the present invention when considered in connection with the figures, wherein like reference numbers refer to similar items throughout the figures and:

DETAILED DESCRIPTION

The following description and the drawings illustrate specific embodiments of the invention sufficiently to enable those skilled in the art to practice them. Other embodiments may incorporate structural, logical, electrical, process, and other changes. Examples merely typify possible variations. Individual components and functions are optional unless explicitly required, and the sequence of operations may vary. Portions and features of some embodiments may be included in or substituted for those of others. The scope of embodiments of the invention encompasses the full ambit of the claims and all available equivalents of those claims.

Figure 1A:
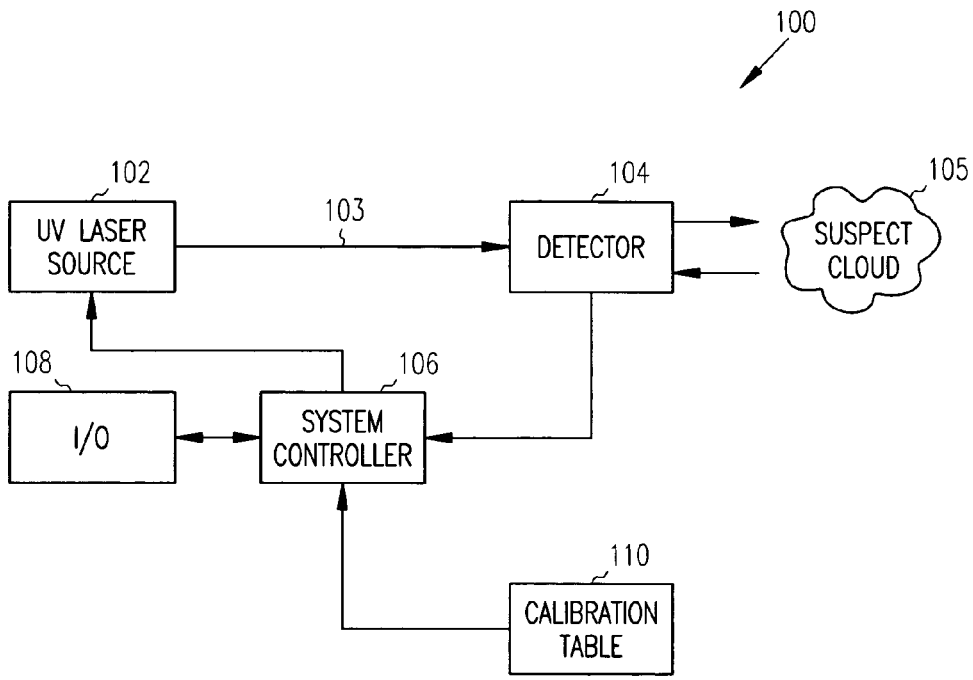
FIG. 1A is a functional block diagram of a bioagent-detection system in accordance with some embodiments of the present invention.

FIG. 1A is a functional block diagram of a bioagent-detection system in accordance with some embodiments of the present invention. Bioagent-detection system 100 may be used to detect many common biological agents, including bacteria and viruses, which have aromatic-protein shells. An example of an aromatic-protein shell is Tryptophan, although the scope of the invention is not limited in this respect. Examples of these biological agents may include Anthrax, Botox, Staphylococcal Enterotoxin B, and Clostridium Perfringens, although the scope of the invention is not limited in this respect. The proteins of their aromatic-protein shells fluoresce at a particular ultraviolet wavelength when excited. Thus by exciting these proteins and measuring their fluorescence, the level of these proteins may be determined. The detection of elevated levels of a protein, such as Tryptophan, may indicate the presence of bioagent.

In accordance with some embodiments of the present invention, bioagent-detection system 100 comprises laser source 102 to generate laser light 103 at more than one ultraviolet wavelength, and detector 104 to detect a received fluorescence level of aromatic proteins in the atmosphere resulting from the transmission of the ultraviolet wavelengths. The ultraviolet wavelengths may be selected to excite the aromatic protein below an emission peak of the aromatic protein. For example, a fluorescence peak of the Tryptophan occurs at an ultraviolet wavelength of about 345 nm and the ultraviolet wavelengths generated by source 102 to excite Tryptophan may include wavelengths ranging between approximately 270 and 340 nanometers (i.e., below the emission peak of the Tryptophan).

Detector 104 may detect the laser-induced fluorescence level of the aromatic protein in the atmosphere resulting from excitation by the ultraviolet wavelengths. In some embodiments, a detected fluorescence level greater than an ambient or expected atmospheric level may indicate the presence of the biological agent. In some embodiments, detector 104 may comprise avalanche photo diodes for detecting the ultraviolet-induced fluorescence of the excited aromatic protein.

Ultraviolet avalanche photo diodes are an efficient way to detect an ultraviolet fluorescence signal since avalanche photo diodes comprise solid-state detectors with sensitivities comparable to photo-multiplier tubes (PMT) configured for ultraviolet detection. In some alternate embodiments, one or more photo-multiplier tubes configured for ultraviolet detection may be used as part of detector 104.

In some embodiments, bioagent-detection system 100 further comprises system controller 106 to receive a detection signal from detector 104. The detection signal may be approximately proportional to the detected fluorescence level. In some embodiments, system controller 106 may generate a notification signal when the detection signal indicates that a threshold is exceeded. The threshold may indicate that a predetermined density of the aromatic protein is present. In the case of Tryptophan, the predetermined density may be on the order of approximately 1000 particles per liter at a suspect location, although the scope of the invention is not limited in this respect. In some embodiments, the threshold may be based on an ambient or expected level of the aromatic protein in the atmosphere.

In accordance with some embodiments, source 102 may comprise an array of addressable laser diodes for generating the laser light at more than one ultraviolet wavelength. In these embodiments, the array may comprise wavelength-diverse laser diodes for selectively generating a plurality of different ultraviolet wavelengths. The array of addressable laser diodes may comprise a plurality of groups of diodes in which each group is selectable to generate a single predetermined ultraviolet wavelength. The wavelengths may be in a range which may cause an aromatic protein, such as Tryptophan, to fluoresce.

In some embodiments, system controller 106 may be configured to substantially simultaneously address the different wavelength diodes of the array to generate more than one ultraviolet wavelength substantially simultaneously. System controller 106 may determine whether the detected fluorescence level resulting from the substantially simultaneous transmission of more than one ultraviolet wavelength indicates that the aromatic protein exceeds an ambient atmospheric level. In some embodiments, a user may instruct system 100 through I/O 108 to configure system controller 106 to substantially simultaneously address the different wavelength diodes of the array to generate more than one ultraviolet wavelength substantially simultaneously. When the aromatic protein does not exceed an ambient atmospheric level by a predetermined amount, system controller 106 may determine that bioagents are not likely to be present, and may provide an indication to the user through I/O 108.

When the aromatic protein exceeds an ambient atmospheric level by a predetermined amount, system controller 106 may indicate that bioagents may be present, and system controller 106 may provide an initial indication to the user through I/O 108. This initial indication may indicate a "hot-spot", and in this situation, further detection steps may be performed to help reduce false alarms. In these embodiments, system controller 106 may address a first group of diodes of the array to generate ultraviolet laser light at a first wavelength. Detector 104 may receive a detected fluorescence level resulting from the fluorescence induced by the first wavelength. System controller 106 may then address a second group of diodes of the array to generate ultraviolet laser light at a second wavelength and detector 104 may receive a detected fluorescence level resulting from the fluorescence induced by the second wavelength. System controller 106 may correlate these detected fluorescence levels with atmospheric absorption levels for the aromatic protein at the first and second wavelengths to determine if an ambient threshold is exceeded by a predetermined amount. In some embodiments, the atmospheric absorption levels for one or more aromatic proteins may be stored in calibration table 110.

In some other embodiments, system controller 106 may step through a range of wavelengths which cause the aromatic protein to fluoresce. In these embodiments, each wavelength may be transmitted and a level of fluoresce may be detected and compared with atmospheric absorption levels for that wavelength.

In some embodiments, the first and second wavelengths may be a pair of wavelengths, and system controller 106 may repeat the addressing and correlating for diodes of other pairs of wavelengths in a range of wavelengths which cause the aromatic protein to fluoresce. System controller 106 may determine when a bioagent is likely to be present from the correlated detected fluorescence levels resulting from the fluorescing. In some embodiments, the pairs of wavelengths may be separated in wavelength by approximately between one and five nanometers, although the scope of the present invention is not limited in this respect.

These multi-wavelength differential laser-induced fluorescence techniques implemented by various embodiments of the present invention may help eliminate false alarms which may result from naturally occurring aerosols and aromatic proteins. In some embodiments, the laser diodes, which may be part of source 102, may be selected to generate specific ultraviolet wavelengths to within a couple of nanometers. In some embodiments, conventional laser diodes may be fabricated with larger energy bandgaps to operate at very short wavelengths (i.e., ultraviolet).

In some embodiments, system 100 may comprise other functional elements to perform transmit and receive operations including the separation of the transmitted and received wavelengths. In some embodiments, system 100 may comprise a collimator to collimate laser light 103 provided by source 102. The collimator may collimate the laser light for direction toward suspect cloud 105, which may have an aromatic protein. In some embodiments, the collimator may comprise a lens to direct the received wavelengths to a detection element, such as avalanche photo diodes, although the scope of the invention is not limited in this respect.

In some embodiments, system 100 may further comprise a range finder to determine a distance to suspect cloud 105 which may contain an aromatic protein. System controller 106 may use the distance to determine thresholds for detection based on an absorption-wavelength curve for the aromatic protein.

In alternate embodiments, rather than an array of wavelength selectable laser diodes, source 102 may comprise a tunable-fiber laser to generate more than one ultraviolet wavelength. This is described in more detail below. In some embodiments, system 100 may be a hand-held standoff bioagent detector having a compartment adapted to receive batteries for supplying power to at least source 102, detector 104 and system controller 106.

In some embodiments, the detection of Tryptophan with system 100 may serve as an initial first warning. Once the determination of a "hot spot"—an unusually high concentration of Tryptophan—is detected (e.g., above the natural occurring concentrations), then a sample may be collected and taken to a laboratory (in some cases a mobile laboratory) for identification of the biological agent, although the scope of the invention is not limited in this respect.

Although system 100 is illustrated as having several separate functional elements, one or more of the functional elements may be combined and may be implemented by combinations of software-configured elements, such as processing elements including digital signal processors (DSPs), and/or other hardware elements. For example, system controller 106 may comprise one or more microprocessors, DSPs, application specific integrated circuits (ASICs), and combinations of various hardware and logic circuitry for performing at least the functions described herein.

Figure 1B:
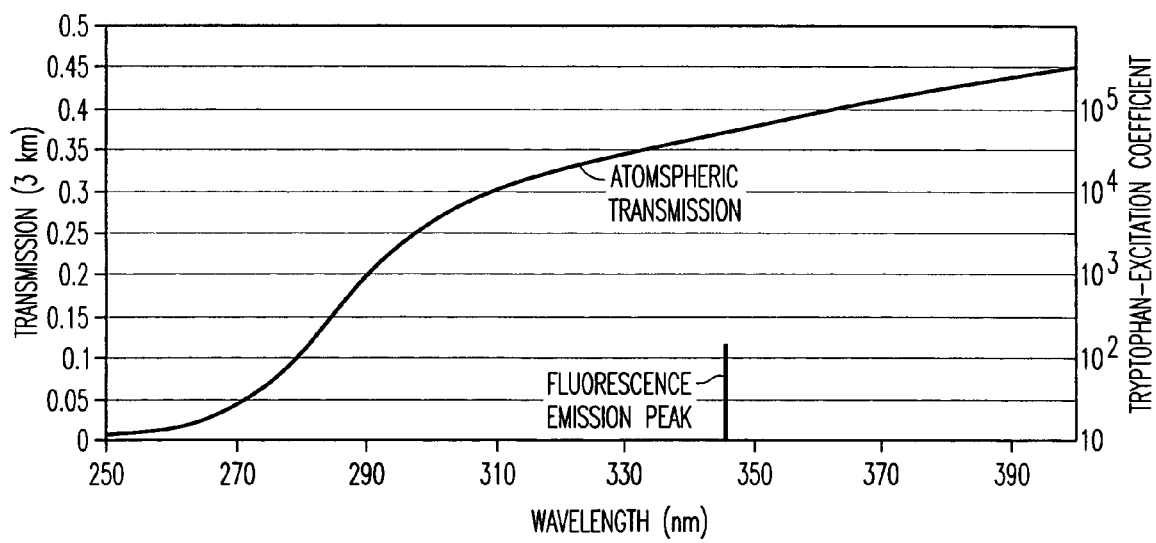
FIG. 1B illustrates atmospheric absorption of Tryptophan as a function of wavelength.

FIG. 1B illustrates atmospheric absorption of Tryptophan as a function of wavelength. In accordance with some embodiments of the present invention, the gradual variation of absorption as a function of wavelength shown in FIG. 1B may be used to decouple variations in the atmospheric absorption as well as the variations in the absolute power of the emitting diodes of source 102. In these embodiments, Tryptophan may be substantially simultaneously excited at two different wavelengths that are sufficiently separated in wavelength so that the different absorption efficiency can be determined. The two different wavelengths may be sufficiently close so that atmospheric variations do not significantly affect one more so than the other. In these embodiments, the resultant differential absorption and subsequent fluorescence return signal may provide a more robust determination of the concentration level of Tryptophan.

In some embodiments, a rapid sequential illumination with a differential pair of wavelengths is performed so that the selected signal can be resolved in time and correlated to the particular emission/excitation wavelength. In this way, the differential absorption may provide for a more robust detection.

In some embodiments, a calibration process may be performed. For example, in a controlled environment, system 100 may be tested against known Tryptophan concentrations in a test chamber and/or at test range facility. During calibration, different wavelengths may be emitted and the corresponding Tryptophan fluorescence may be measured and inputted into calibration table 110. In some embodiments, the calibration may comprise measuring the emission wavelength of diodes of source 102, and measuring the power of the emission at each wavelength. In these embodiments, the calibration may also comprise measuring the fluorescence return signal from a controlled known fluorescence source at each wavelength, and measuring the fluorescence signal strength from simultaneous multiple diode illuminations, which may be used as part of an initial illumination/interrogation protocol. In some embodiments, the calibration may also comprise measuring emission transmissions in a variety of controlled atmospheric scenarios (e.g., humidity, obscuration, etc.).

Figure 2:
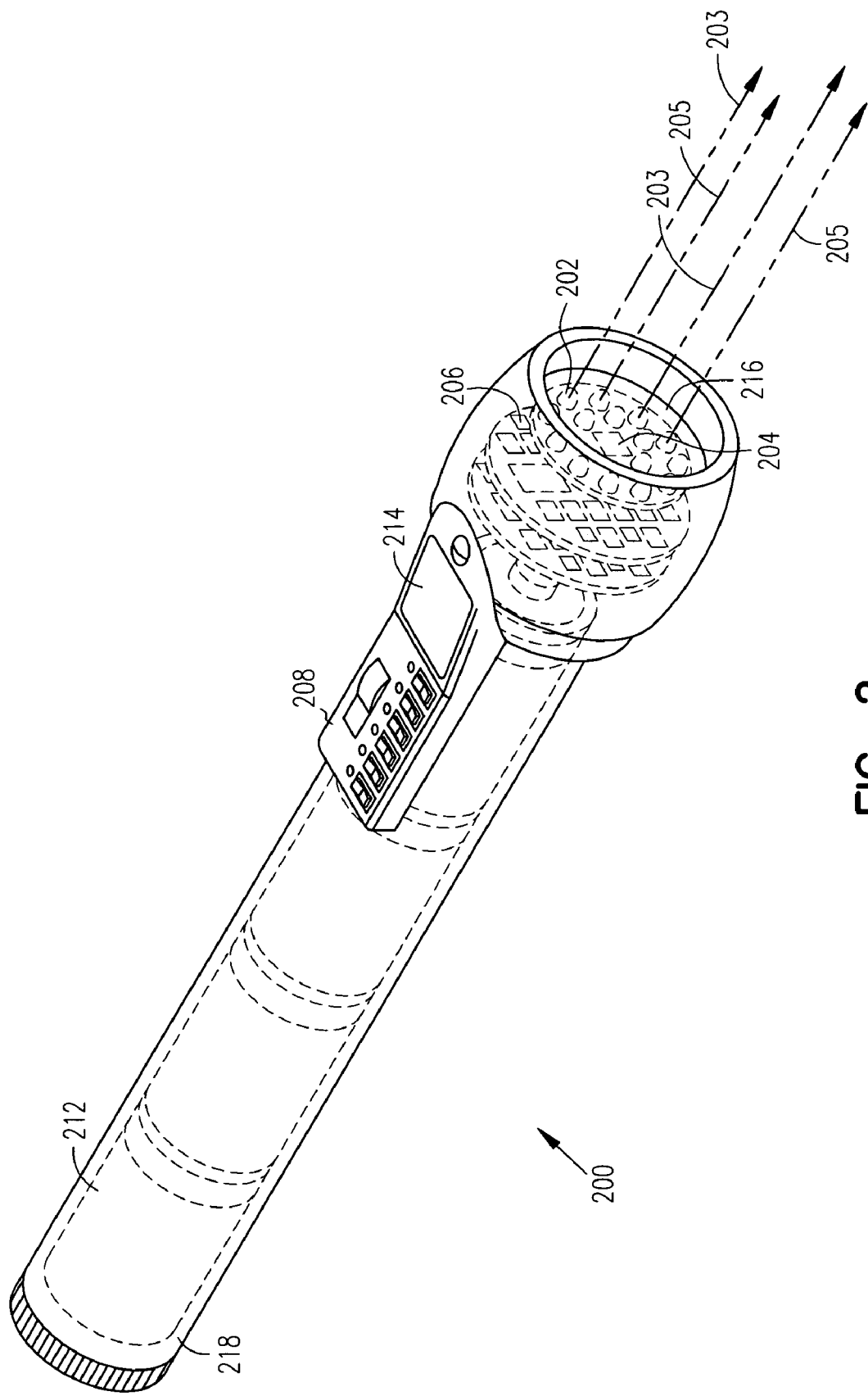
FIG. 2 illustrates a hand-held standoff bioagent detector in accordance with some embodiments of the present invention.

FIG. 2 illustrates a hand-held standoff bioagent detector in accordance with some embodiments of the present invention. Hand-held bioagent detector 200 may be suitable for use as bioagent-detection system 100 (FIG. 1A), although other systems are also suitable. Hand-held bioagent detector 200 may comprise an array of wavelength-diverse laser diodes 202 for selectively generating individual ultraviolet wavelengths which may cause an aromatic protein to fluoresce. Hand-held bioagent detector 200 may also comprise detector 204 to receive a fluorescence level induced by the laser light, as well as other circuitry 206. Hand-held bioagent detector 200 may also comprise I/O 208 with display 214.

In embodiments, array of laser diodes 202 may correspond to source 102 (FIG. 1A), detector 204 may correspond to detector 104 (FIG. 1A), and other circuitry 206 may correspond to system controller 106 (FIG. 1A) and calibration table 110 (FIG. 1A), although the scope of the invention is not limited in this respect. Hand-held bioagent detector 200 may further comprise lens 216 to collimate the laser light provided by diodes 202 for direction toward a suspect cloud of aromatic protein. Lens 216 may also direct received fluoresce wavelengths to detector 204. In some embodiments, lens 216 may be a common aperture with a small F# configured for laser-induced fluorescence detection, although the scope of the invention is not limited in this respect.

Hand-held bioagent detector 200 may also have compartment 218 adapted to receive batteries 212 for supplying power to elements of the detector. In some embodiments, a user may use I/O 208 to select a broad-band illumination, or select a sequential pulsing of individual or pairs of laser diodes 202. Hand-held bioagent detector 200 is illustrated as transmitting ultraviolet wavelength 203 ($\lambda_n$) and ultraviolet wavelength 205 ($\lambda_n + \Delta\lambda_n$). Ultraviolet wavelength 205 may include a calibrated wavelength offset ($\Delta\lambda_n$). In embodiments, system 200 may detect small signal differences between the differential absorptions and detector 204 may operate in a signal-subtraction mode.

In some embodiments, differential absorption and subtraction comprises exciting the Tryptophan at wavelengths where different absorption exists at a known pre-determined (i.e., calibrated) level. The resultant fluorescence signal may accordingly also be at a different level, which may also be known from the calibration. The subtraction of the fluorescence signals may help determine the existence of Tryptophan by testing against the calibrated differential value which may be stored in a look up table, such as calibration table 110 (FIG. 1A). Differential signal subtraction may help facilitate robust sensing in a variety of atmospheric conditions because, among other things, large variations of common background signals may be decoupled.

Figure 3:
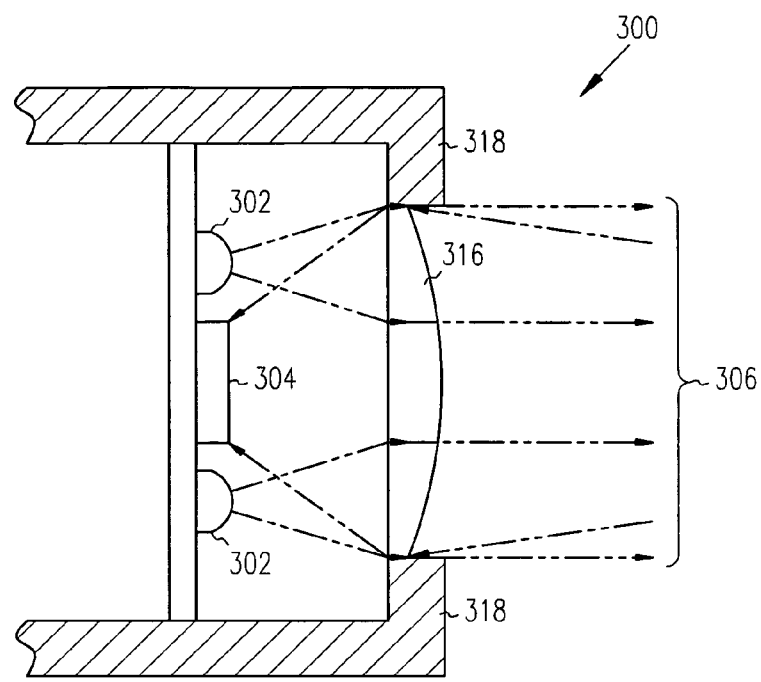
FIG. 3 illustrates a portion of a bioagent-detection system in accordance with some embodiments of the present invention.

FIG. 3 illustrates a portion of a bioagent-detection system in accordance with some embodiments of the present invention. Portion 300 may be suitable for use as part of hand-held bioagent detector 200 (FIG. 2), although other elements may also be suitable for use. Portion 300 includes array of laser diodes 302 for generating one or more ultraviolet wavelengths, and lens 316 for collimating the ultraviolet wavelengths. In some embodiments, lens 316 may provide collimated wavefront 306 although the scope of the invention is not limited in this respect. Portion 300 may also include detector 304 for receiving ultraviolet wavelengths resulting from the fluorescence induced on an aromatic protein by the wavelengths transmitted from diodes 302. Portion 300 is also illustrated as including a portion of housing 318.

In accordance with some embodiments, diodes 302 may correspond to diodes 202 (FIG. 2), detector 304 may correspond to detector 204 (FIG. 2), lens 316 may correspond to lens 216 (FIG. 2) and housing 318 may correspond to housing 218 (FIG. 2), although the scope of the invention is not limited in this respect.

In some embodiments, transmit and receive optics may be positioned to provide light collection in a coaxial configuration. In these embodiments, detector 304 may be positioned centrally to allow fast-collection optics to facilitate a high sensitivity of detection. Diodes 302 may share a receive aperture so that the emission light may exit in a substantially collimated form. In these embodiments, diodes 302 may be individually designed based on the window or lens specification.

Figure 4:
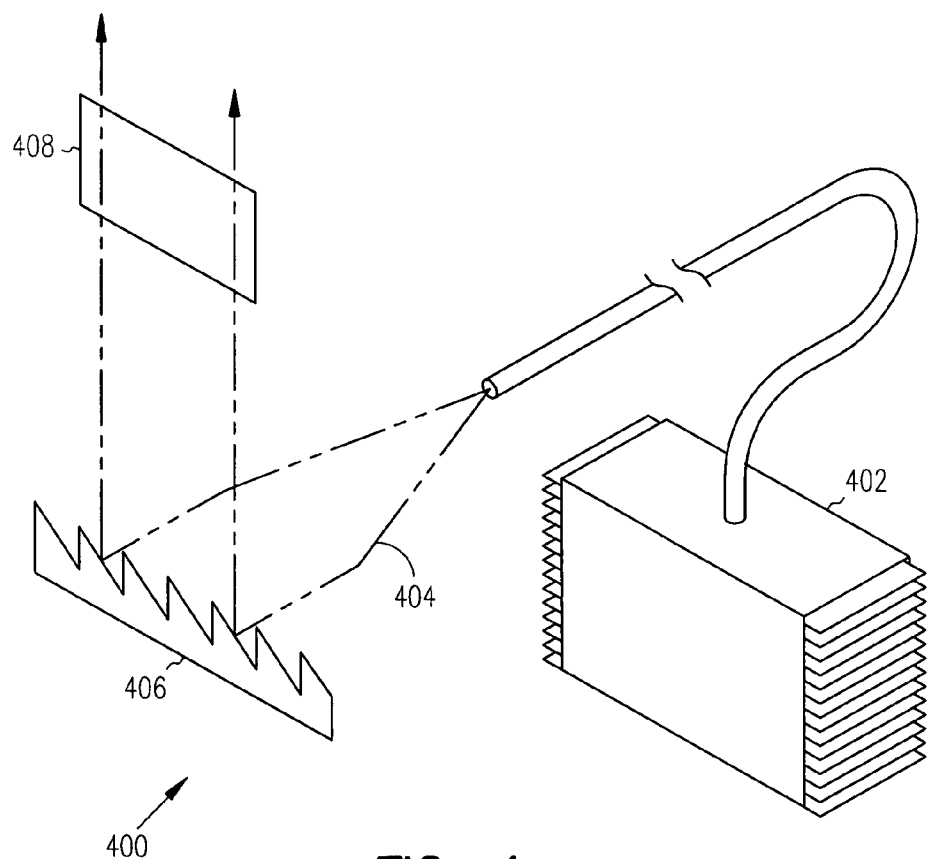
FIG. 4 illustrates a tunable fiber-laser source for use with some alternate embodiments of the present invention.

FIG. 4 illustrates a tunable fiber-laser source for use with some alternate embodiments of the present invention. Tunable fiber-laser source system 400 may be suitable for use as source 102 (FIG. 1A), although other ultraviolet laser sources may also be suitable. In some embodiments, source system 400 may comprise a compact solid-state Cerium laser, which may be tunable to wavelengths that may induce fluorescence in an aromatic protein, such as Tryptophan. In some embodiments, tunable fiber-laser source system 400 may comprise diode assembly 402 to generate ultraviolet wavelengths, and inter-cavity collimating optics 404 to collimate the wavelengths and provide a collimated wavefront to intracavity tuning element 406. In some embodiments, intracavity tuning element 406 may comprise a grating such as a Blaze grating, although the scope of the invention is not limited in this respect. Intracavity tuning element 406 may be tuned to selectively provide a particular ultraviolet wavelength through output coupler 408. In embodiments in which intracavity tuning element 406 comprises a grating, the grating may be angled to selectively provide a particular ultraviolet wavelength through output coupler 408. Output coupler 408 may provide the particular ultraviolet wavelength which may be directed toward a suspect aromatic protein cloud. In some embodiments, output coupler 408 may also receive the induced fluorescence wavelength and direct the induced fluorescence wavelength to a detector.

Figure 5:
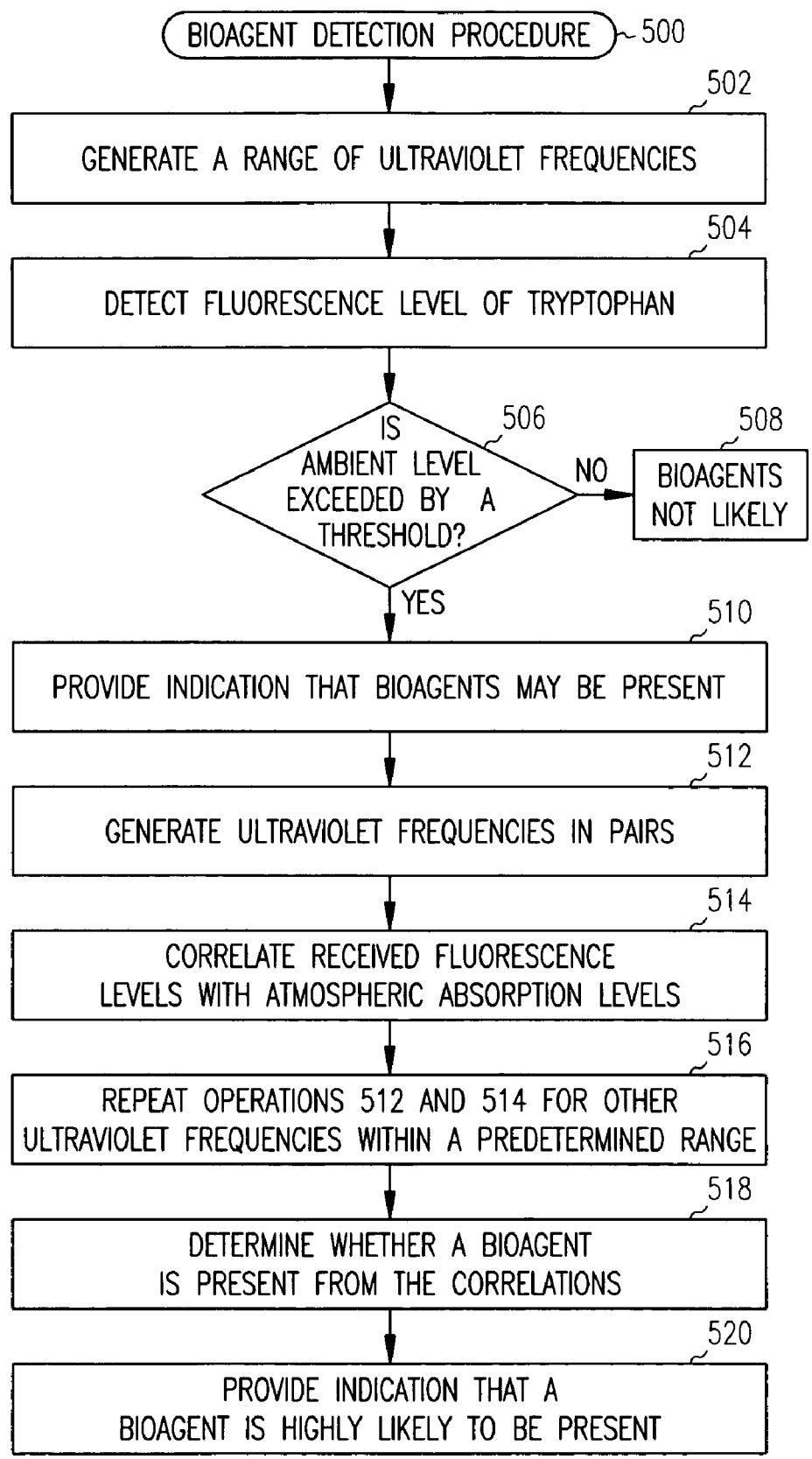
FIG. 5 is a flow chart of a bioagent-detection procedure in accordance with some embodiments of the present invention.

FIG. 5 is a flow chart of a bioagent-detection procedure in accordance with some embodiments of the present invention. Bioagent detection procedure 500 may be used to detect the presence of bioagents in a standoff mode. In some embodiments, bioagent detection procedure 500 may provide an initial indication of whether a hot spot exists, and may further determine whether bioagents are highly likely to be present. Bioagent detection procedure 500 may be performed by a bioagent-detection system, such as system 100 (FIG. 1A), although other systems may also be suitable.

In operation 502, a range of ultraviolet wavelengths are generated to provide broad-band illumination. Operation 502 may be performed by an array of laser diodes, such as the diodes of source 102 (FIG. 1A), selected to simultaneously generate a plurality of different ultraviolet wavelengths which cause an aromatic protein to fluoresce. In other embodiments, operation 502 may be performed by a tunable laser source, such as source system 400 (FIG. 4), which may generate different wavelengths over a short period of time.

Operation 504 detects the fluorescence level of an aromatic protein resulting from the different wavelengths generated in operation 502. Operation 504 may be performed by a detector, such as detector 104 (FIG. 1A).

Operation 506 determines when the detected fluorescence level of an aromatic protein exceeds an ambient level by a threshold. When the threshold is not exceeded, operation 508 may provide an indication to a user that bioagents are not likely present. When the threshold is exceeded, operation 510 may provide an indication to a user that bioagents may be present. Operations 506, 508 and 510 may be performed by a system controller, such as system controller 106 (FIG. 1A).

In operation 512, pairs of ultraviolet wavelengths may be generated and directed toward a location where bioagents are suspected. In some embodiments, operation 512 may sequentially generate a first ultraviolet wavelength ($\lambda_n$) and a second ultraviolet wavelength ($\lambda_n + \Delta\lambda_n$). The second ultraviolet wavelength may include a calibrated wavelength offset ($\Delta\lambda_n$).

In operation 514, the received fluorescence levels from the transmitted pairs of wavelengths may be correlated with ambient or expected atmospheric levels. In some embodiments, operation 514 may detect small signal differences between the differential absorptions and may operate in a signal-subtraction mode.

Operation 516 may repeat operations 512 and 514 for other wavelengths within a range of wavelengths which cause the aromatic protein to fluoresce, and operation 518 may determine whether a bioagent is highly likely to be present based on the correlations of the repeating of operation 514.

When operation 518 determines that the presence of a bioagent is highly likely, operation 520 may provide an indication to a user indicating that a bioagent is highly likely to be present. When operation 518 determines that the presence of a bioagent is not highly likely, operation 520 may provide an indication to a user indicating that a bioagent is not highly likely to be present.

In some embodiments, procedure 500 may include determining a distance to a suspect cloud. The distance along with atmospheric absorption levels may be used in operations 506 and 518 to determine expected florescence levels and thresholds.

In some embodiments, rather than generating pairs of wavelengths, operations 512 and 514 may be repeated to generate individual wavelengths to fluoresce the aromatic protein. In these embodiments, operation 518 may correlate the received fluoresce to determine whether a bioagent is highly likely to be present.

Although the individual operations of procedure 500 are illustrated and described as separate operations, one or more of the individual operations may be performed concurrently and nothing requires that the operations be performed in the order illustrated.

Thus, systems and methods that provide bioagent detection have been described. Standoff bioagent-detection systems and methods that permit bioagent detection without the need to be present within the potential biological threat have also been described. Bioagent-detection systems and methods that may be more accurate and may have lower false-alarm rates have also been described. Bioagent-detection systems and methods that are compact, efficient and robust, and may be implemented in hand-held devices have also been described.

It is emphasized that the Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features that are expressly recited in each claim. Rather, as the following claims reflect, inventive subject matter lies in less than all features of a single disclosed embodiment. Thus the following claims are hereby incorporated into the detailed description, with each claim standing on its own as a separate preferred embodiment.

What is claimed is:

1. A standoff bioagent detection system comprising:
a detector to detect a fluorescence level; and
a controller configured to initially cause a plurality of laser diodes to generate a range of ultraviolet wavelengths;
wherein when the detector detects that a fluorescence level of an aromatic protein resulting from the range ultraviolet wavelengths exceeds a threshold, the controller is further configured to:
address selected pairs of the laser diodes to alternately generate first and second ultraviolet wavelengths by sequentially pulsing the selected pairs in rapid succession, both the first and second wavelengths selected to fluoresce the detected aromatic protein; and resolve in time and separately correlate detected fluorescence levels resulting from sequential transmission of the first and second ultraviolet wavelengths to determine a differential absorption level, wherein the second ultraviolet wavelength and the first ultraviolet wavelength are separated by no more than approximately five nanometers.

2. The standoff bioagent detection system of claim 1 wherein the controller is further configured to compare the differential absorption level with a calibrated differential value to determine whether an elevated level of a predetermined aromatic protein is present, wherein the selected pairs of the laser diodes are selected to separately generate first and second ultraviolet wavelengths to fluoresce the predetermined aromatic protein, wherein the calibrated wavelength offset is selected so that both the first and second ultraviolet wavelengths have similar atmospheric absorption levels, and wherein the first and second wavelengths are between approximately 270 and 340 nanometers.

3. The standoff bioagent detection system of claim 2 wherein the laser diodes comprise an addressable array of laser diodes, wherein the first and second ultraviolet wavelengths comprise a pair of ultraviolet wavelengths, and wherein the controller is further configured to repeat the addressing, the resolving in time and the correlation for other pairs of ultraviolet wavelengths to detect corresponding other aromatic proteins based on differential absorption levels.

4. A method to detect bioagents using differential absorption comprising:

generating a range of ultraviolet wavelengths with a plurality of laser diodes; and detecting a fluorescence level of an aromatic protein in response to the generating, wherein when a detected fluorescence level of an aromatic protein resulting from the range ultraviolet wavelengths exceeds a threshold, the method further comprises:

addressing selected pairs of the laser diodes to alternately generate first and second ultraviolet wavelengths by sequentially pulsing the selected pairs in rapid succession, both the first and second wavelengths selected to fluoresce the detected aromatic protein; and resolving in time and separately correlating detected fluorescence levels resulting from sequential transmission of the first and second ultraviolet wavelengths to determine a differential absorption level, wherein the second ultraviolet wavelength and the first ultraviolet wavelength are separated by no more than approximately five nanometers.

5. The method of claim 4 further comprising comparing the differential absorption level with a calibrated differential value to determine whether an elevated level of a predetermined aromatic protein is present, wherein the selected pairs of the laser diodes are selected to separately generate first and second ultraviolet wavelengths to fluoresce the predetermined aromatic protein, wherein the calibrated wavelength offset is selected for so that both the first and second ultraviolet wavelengths have similar atmospheric absorption levels, and wherein the first and second wavelengths are between approximately 270 and 340 nanometers.

6. The method of claim 5 wherein the laser diodes comprise an addressable array of laser diodes, wherein the first and second ultraviolet wavelengths comprise a pair of ultraviolet wavelengths, and wherein when the detected fluorescence level resulting from the range ultraviolet wavelengths exceeds the threshold, the method further comprises repeating the addressing, the resolving in time and the correlating for other pairs of ultraviolet wavelengths to detect corresponding other aromatic proteins based on differential absorption levels.

* * * * *